United States Patent
Scott

(10) Patent No.: US 11,607,353 B2
(45) Date of Patent: Mar. 21, 2023

(54) SUPER COMFORT MAXI PAD

(71) Applicant: Janice D. Scott, Lithia Springs, GA (US)

(72) Inventor: Janice D. Scott, Lithia Springs, GA (US)

(*) Notice: Subject to any disclaimer, the term of this patent is extended or adjusted under 35 U.S.C. 154(b) by 216 days.

(21) Appl. No.: 16/974,140

(22) Filed: Dec. 2, 2020

(65) Prior Publication Data

US 2022/0087880 A1  Mar. 24, 2022

Related U.S. Application Data

(60) Provisional application No. 63/204,288, filed on Sep. 24, 2020.

(51) Int. Cl.
| | |
|---|---|
| A61F 13/53 | (2006.01) |
| A61F 13/472 | (2006.01) |
| A61F 13/56 | (2006.01) |
| A61F 13/47 | (2006.01) |
| A61F 13/84 | (2006.01) |

(52) U.S. Cl.
CPC ...... *A61F 13/5611* (2013.01); *A61F 13/4704* (2013.01); *A61F 13/47272* (2013.01); *A61F 13/53* (2013.01); *A61F 13/5616* (2013.01); *A61F 2013/8402* (2013.01)

(58) Field of Classification Search
CPC .. A61F 13/5611; A61F 13/53; A61F 13/5616; A61F 2013/8402; A61F 13/4708; A61F 13/47; A61F 13/472; A61F 13/476
See application file for complete search history.

(56) References Cited

U.S. PATENT DOCUMENTS

| | | | | |
|---|---|---|---|---|
| 4,946,454 | A * | 8/1990 | Schmidt | A61F 13/47272 604/386 |
| 5,429,630 | A * | 7/1995 | Beal | A61F 13/476 604/389 |
| 5,545,156 | A * | 8/1996 | DiPalma | A61F 13/51401 604/378 |
| 5,752,947 | A * | 5/1998 | Awolin | A61F 13/4753 604/385.04 |
| 8,231,591 | B2 * | 7/2012 | Woltman | A61F 13/4704 604/385.01 |
| 2004/0158221 | A1 * | 8/2004 | Mizutani | A61F 13/55165 604/385.17 |
| 2006/0230505 | A1 * | 10/2006 | Martz | A61F 13/472 2/400 |

FOREIGN PATENT DOCUMENTS

JP           07000447 A *  1/1995  ........... A61F 13/472

* cited by examiner

*Primary Examiner* — Daniel J Colilla

(57) ABSTRACT

This invention relates to a disposable sanitary napkin having longitudinal curved edges and transverse ends having at least one compression line extending a long and close to the longitudinal edges, such that the pressure of the user's thighs on the product will bring about a protuberance of absorbent material towards the perineal area when worn. The product of this invention thus bring the absorbent material closer to the discharge of menstrual fluid in the absorbent middle which is the critical cause of leakage from the longitudinal edges of sanitary napkins.

4 Claims, 2 Drawing Sheets

SUPER COMFORT MAXI PAD

DETAILED DESCRIPTION OF THE INVENTION

Figure 1A:
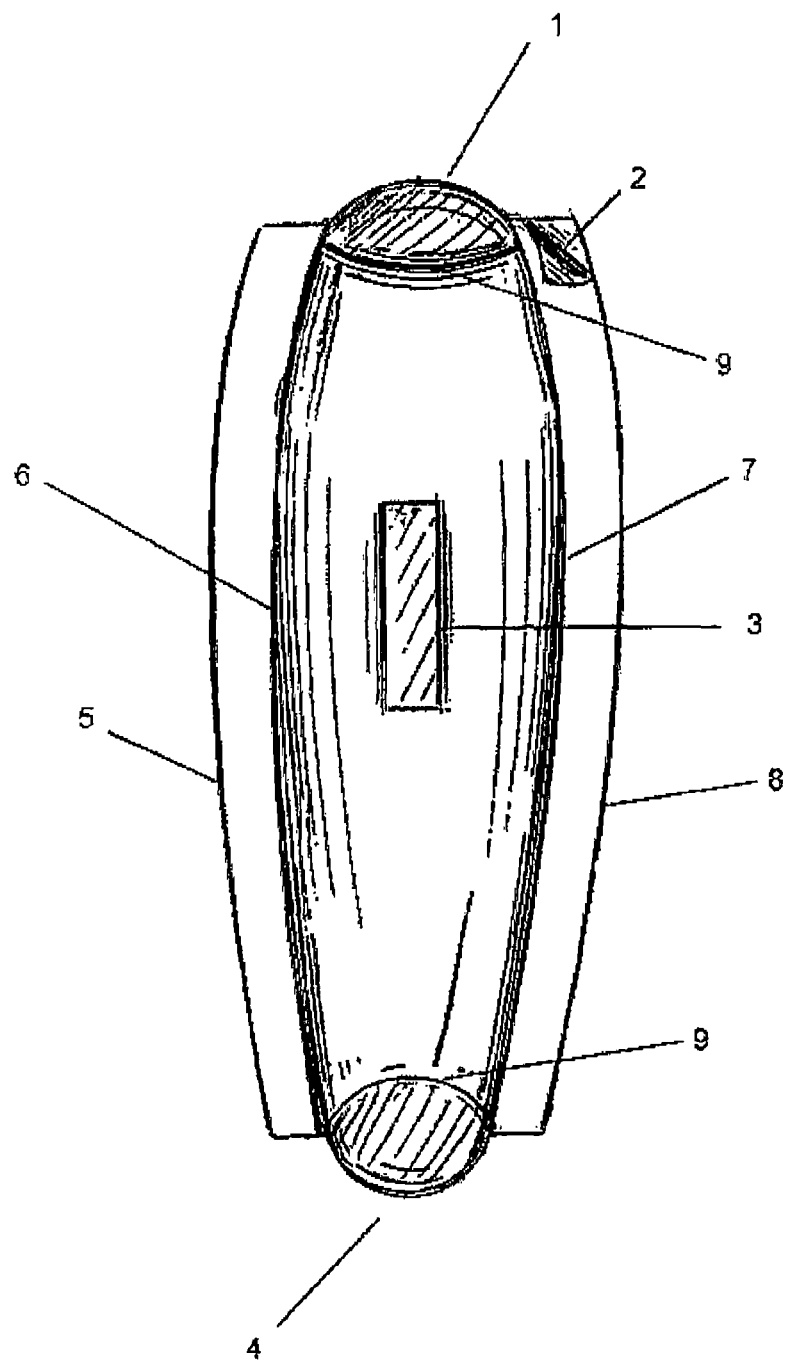
FIG. 1A shows a plan view of the absorbent pad.
Figure 1B:
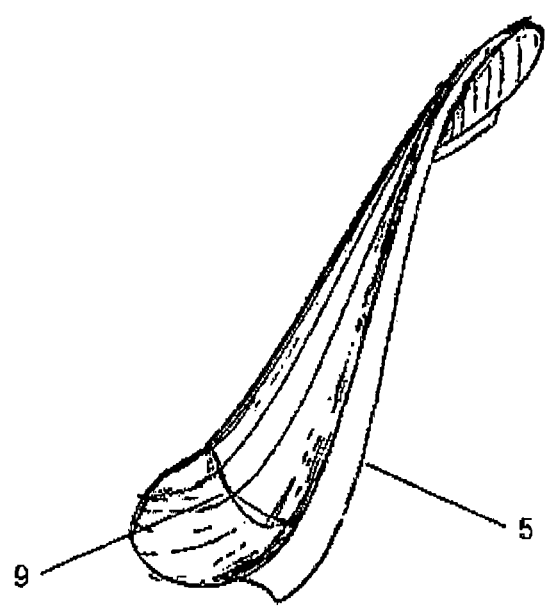
FIG. 1B shows a perspective view of the absorbent pad.

This invention relates to a disposable sanitary napkin or pad having longitudinal curved, ends 1 and 4 and curved transverse edges 6 and 7 having at least one compression line 9 extending along and close to the longitudinal ends, such that the pressure of the user's thighs on the product will bring about a protuberance of absorbent material towards the perineal area when worn. The product of this invention thus bring the absorbent material closer to the discharge of menstrual fluid in an absorbent center section which is the critical cause of leakage from the longitudinal ends of sanitary napkins.

The sanitary napkin or pad, includes curved wings 8 and is disposable. The size and absorbent capacity of the sanitary pad is suitable for average to medium flow. Ultra-thin pad types preferred embodiment for both female comfort and packing space reduction. This pad has an absorbent central section 3 for all stains and side adhesive strips 2 to lock in and around the bottom of the panties to prevent leakage of any fluids. Curved wings 5 locks in freshness and keeps the pad firmly in place with no leakage.

A unit is a pack containing a total of a minimum of 20 pads.

What is claimed:

1. A disposable absorbent article comprising:
   an absorbent pad having:
   a first curved longitudinal end and a second curved longitudinal end;
   a first curved side edge and a second curved side edge;
   a first compression line extending adjacent to the first curved longitudinal end completely across the entire absorbent article from the first curved side edge to the second curved side edge, wherein the first compression line is a curved line with a concave side facing the first curved longitudinal end;
   a second compression line extending adjacent to the second curved longitudinal end completely across the entire absorbent article from the first curved side edge to the second curved side edge, wherein the second compression line is a curved line with a concave side facing the second curved longitudinal end;
   wherein the pad is configured to bend along the first and second compression lines when the disposable absorbent article is pressed by a user's thighs thereby causing the first curved longitudinal end to protrude towards a perineal area of the user.

2. The disposable absorbent article according to claim 1, further comprising:
   a first curved wing adjacent the first curved side edge of the absorbent pad; and
   a second curved wing adjacent the second curved side edge of the absorbent pad.

3. The disposable absorbent article according to claim 2, further comprising:
   a first adhesive strip that extends along the first wing; and
   a second adhesive strip that extends along the second wing,
   wherein the average pad thickness is less than 2 mm.

4. The disposable absorbent article according to claim 1, wherein the absorbent pad has an absorbent central portion.

* * * * *